United States Patent
Tokuchi et al.

(10) Patent No.: US 11,717,191 B2
(45) Date of Patent: Aug. 8, 2023

(54) INFORMATION PROCESSING APPARATUS AND NON-TRANSITORY COMPUTER READABLE MEDIUM

(71) Applicant: AGAMA-X Co., Ltd., Tokyo (JP)

(72) Inventors: Kengo Tokuchi, Tokyo (JP); Masahiro Sato, Tokyo (JP)

(73) Assignee: Agama-X Co., Ltd., Tokyo (JP)

( * ) Notice: Subject to any disclaimer, the term of this patent is extended or adjusted under 35 U.S.C. 154(b) by 515 days.

(21) Appl. No.: 16/853,869

(22) Filed: Apr. 21, 2020

(65) Prior Publication Data

US 2021/0186379 A1 Jun. 24, 2021

(30) Foreign Application Priority Data

Dec. 19, 2019 (JP) ................................. 2019-228992

(51) Int. Cl.
| | | |
|---|---|---|
| A61B 5/12 | (2006.01) | |
| H04R 25/00 | (2006.01) | |
| A61B 5/00 | (2006.01) | |
| A61B 5/38 | (2021.01) | |

(52) U.S. Cl.
CPC ............... *A61B 5/125* (2013.01); *A61B 5/38* (2021.01); *A61B 5/4836* (2013.01); *A61B 5/7282* (2013.01); *H04R 25/55* (2013.01); *H04R 2225/55* (2013.01)

(58) Field of Classification Search
None
See application file for complete search history.

(56) References Cited

U.S. PATENT DOCUMENTS

2008/0205660 A1* 8/2008 Goldstein ............... G01H 3/14
  381/60
2012/0300964 A1* 11/2012 Ku ........................ A61B 5/125
  381/321

FOREIGN PATENT DOCUMENTS

| JP | 2004065518 A | * | 3/2004 |
|---|---|---|---|
| JP | 2004-185563 A | | 7/2004 |
| JP | 2005-295175 A | | 10/2005 |
| JP | 2010-200258 A | | 9/2010 |
| WO | 2009/125579 A1 | | 10/2009 |
| WO | 2010/061539 A1 | | 6/2010 |

OTHER PUBLICATIONS

Peter M. Rabinowitz, Noise-Induced Hearing Loss, 61 Am. Fam'y Physician 2749 (May 1, 2000) (Year: 2000).*

* cited by examiner

*Primary Examiner* — Walter F Briney, III
(74) *Attorney, Agent, or Firm* — Hoffman Warnick LLC (57) ABSTRACT

An information processing apparatus includes a processor. The processor is configured to output a caution, based on an operation history of a device, the device being worn by a user and emitting sound, and on a judging result regarding whether biological information concerning the user satisfies a condition for hearing loss.

20 Claims, 2 Drawing Sheets

FIG. 4

| ID | DEVICE NAME | OPERATION HISTORY |
|---|---|---|
| 1 | A | · TOTAL OPERATION TIME<br>· OPERATION TIME BY VOLUME LEVEL<br>· SETTINGS OF SOUND RANGE<br>· PLAYBACK CONTENT<br>. . . |
| . . . | . . . | . . . |

FIG. 5

| ID | USER | GENDER | AGE | MEDICAL HISTORY |
|---|---|---|---|---|
| 1 | α | MALE | 50 | . . . |
| . . . | . . . | . . . | . . . | . . . |

FIG. 6

| ID | USER | BEHAVIOR HISTORY |
|---|---|---|
| 1 | α | · DRINKING<br>· SMOKING<br>· EATING<br>· MEDICATION<br>. . . |
| . . . | . . . | . . . |

FIG. 7

INFORMATION PROCESSING APPARATUS AND NON-TRANSITORY COMPUTER READABLE MEDIUM

CROSS-REFERENCE TO RELATED APPLICATIONS

This application is based on and claims priority under 35 USC 119 from Japanese Patent Application No. 2019-228992 filed Dec. 19, 2019.

BACKGROUND

(i) Technical Field

The present disclosure relates to an information processing apparatus and a non-transitory computer readable medium.

(ii) Related Art

Japanese Unexamined Patent Application Publication No. 2004-185563 discloses a reporting device that is used to collect surrounding sound with a built-in microphone and output the collected sound to an earphone under normal conditions.

Japanese Unexamined Patent Application Publication No. 2010-200258 discloses a hearing aid that amplifies sound collected by a hearing aid microphone disposed outside an ear, emits the amplified sound and test sound, and stores test results obtained from the test sound collected by a measuring microphone disposed inside the ear.

International Publication No. 2009/125579 discloses a hearing aid that amplifies hearing aid sound at a first amplification factor and amplifies searching sound at a second amplification factor which is greater than the first amplification factor.

Japanese Unexamined Patent Application Publication No. 2005-295175 discloses a headphone device that enables a user to hear surrounding sound while hearing an audio signal source.

International Publication No. 2010/061539 discloses a hearing aid including a hearing aid processor, a specific sound generator, and a selector. The hearing aid processor executes hearing aid processing on surrounding sound collected by a sound collector. The specific sound generator generates a predetermined signal. Based on the judging result as to whether a main body of the hearing aid has attached to an ear, the selector selects sound subjected to hearing aid processing executed by the hearing aid processor and sound generated by the specific sound generator, and outputs the selected sound to a sound output unit.

SUMMARY

Aspects of non-limiting embodiments of the present disclosure relate to executing processing in accordance with whether a user wearing a sound emitting device has hearing loss.

Aspects of certain non-limiting embodiments of the present disclosure overcome the above disadvantages and/or other disadvantages not described above. However, aspects of the non-limiting embodiments are not required to overcome the disadvantages described above, and aspects of the non-limiting embodiments of the present disclosure may not overcome any of the disadvantages described above.

According to an aspect of the present disclosure, there is provided an information processing apparatus including a processor. The processor is configured to output a caution, based on an operation history of a device, the device being worn by a user and emitting sound, and on a judging result regarding whether biological information concerning the user satisfies a condition for hearing loss.

BRIEF DESCRIPTION OF THE DRAWINGS

An exemplary embodiment of the present disclosure will be described in detail based on the following figures, wherein.

DETAILED DESCRIPTION

Figure 1:
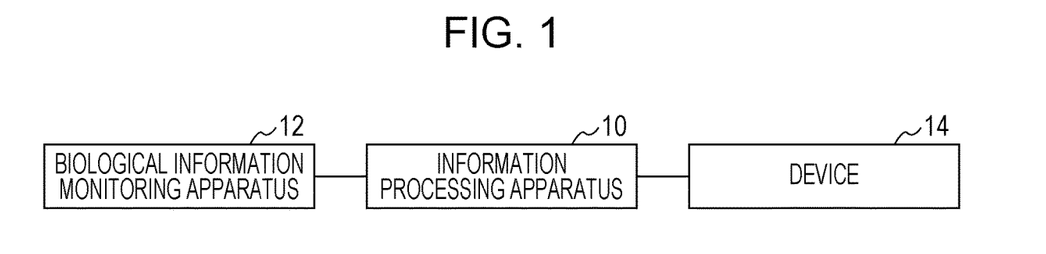
FIG. 1 is a block diagram illustrating an example of the configuration of an information processing system according to the exemplary embodiment.

An information processing system according to the exemplary embodiment will be described below with reference to FIG. 1. FIG. 1 illustrates an example of the configuration of the information processing system according to the exemplary embodiment.

The information processing system according to the exemplary embodiment includes an information processing apparatus 10, one or plural biological information monitoring apparatuses 12, and one or plural devices 14. Only the single information processing apparatus 10, biological information monitoring apparatus 12, and device 14 are shown in FIG. 1, but this configuration is only an example. The information processing system may include an apparatus or/and a device (such as a terminal device and/or a server) other than the information processing apparatus 10, the biological information monitoring apparatus 12, and the device 14 shown in FIG. 1.

Each apparatus or device included in the information processing system is configured to communicate with another apparatus or device included in the information processing system via a wired medium using a cable or a wireless medium. That is, each apparatus or device may be physically connected to another apparatus or device via a cable and send and receive information with each other. Alternatively, each apparatus or device may send and receive information with another apparatus or device by wireless communication. Examples of wireless communication are short-range wireless communication and Wi-Fi (registered trademark). Another wireless communication standard may be employed. Examples of short-range wireless communication are Bluetooth (registered trademark), radio frequency identifier (RFID), and near field communication (NFC). Each apparatus or device may alternatively communicate with another apparatus or device via a communication channel, such as a local area network (LAN) or the Internet.

Examples of the information processing apparatus 10 are a personal computer (hereinafter called a PC), a tablet PC, a smartphone, a cellular phone, and other apparatuses (such as a server, a robot, and another type of device). The information processing apparatus 10 may be a portable terminal device (such as a tablet PC, a smartphone, or a cellular phone), a device placed on a desk or a table, a movable device (such as a self-running device), a device doing some work, or an interactive device which can communicate with people. For example, the information processing apparatus 10 may be a smart speaker having a communication function and including a microphone and a speaker, or a robot interacting with people and doing some work. The information processing apparatus 10 may be a device with artificial intelligence (AI).

The biological information monitoring apparatus 12 is configured to monitor biological information concerning a user. For example, the biological information monitoring apparatus 12 includes various sensors and electrodes, for example, and monitors biological information concerning a user. If multiple biological information monitoring apparatuses 12 are used, they may individually monitor different types of biological information. Alternatively, some or all of the biological information monitoring apparatuses 12 may monitor the same type of biological information. Conversely, the single biological information monitoring apparatus 12 may monitor one type of biological information or multiple types of biological information.

The biological information monitoring apparatus 12 sends monitored biological information to the information processing apparatus 10. Every time the biological information monitoring apparatus 12 monitors biological information, it may send the monitored information to the information processing apparatus 10. The biological information monitoring apparatus 12 may alternatively store monitored biological information and send it to the information processing apparatus 10 at predetermined regular intervals or at a timing given by a user. The biological information monitoring apparatus 12 may receive biological information monitored by another biological information monitoring apparatus 12 and send it together with biological information monitored by the biological information monitoring apparatus 12 to the information processing apparatus 10.

The biological information monitoring apparatus 12 may analyze biological information monitored by the biological information monitoring apparatus 12 or another biological information monitoring apparatus 12 and send information indicating the analysis results to the information processing apparatus 10. The biological information monitoring apparatus 12 may include a processor and the processor may analyze biological information. Biological information may alternatively be analyzed by the information processing apparatus 10 or another apparatus.

The biological information monitoring apparatus 12 may include batteries and be driven by power supplied from the batteries. The biological information monitoring apparatus 12 may alternatively be driven by receiving power from another apparatus, such as the information processing apparatus 10.

The biological information monitoring apparatus 12 may be attached to a user. For example, the biological information monitoring apparatus 12 may be a wearable device that is worn by a user and monitors biological information concerning the user. Specific examples of the biological information monitoring apparatus 12 are a device fixed on the user's head (the forehead, for example), a bearable device attached to the user's ear/ears (such as earphone/ earphones, headphones, or a hearing aid), a device fixed to the user's arm, hand, wrist, or finger (for example, a watch-type device, such as a smart watch), a device put on the user's neck, a device fixed to the user's torso (the abdomen or chest, for example), and a device fixed to the lower limb (the thigh, lower leg, knee, foot, or ankle, for example). The biological information monitoring apparatus 12 may be health equipment fixed to the user's arm, hand, torso, or lower limb. The biological information monitoring apparatus 12 may be attached to another part of the body other than the above-described parts. The biological information monitoring apparatus 12 may be attached to each of multiple parts of the body.

Biological information is physiological information and anatomical information concerning various physiological and anatomical aspects of human bodies. The concept of biological information covers information concerning the brain activities (such as brain waves, brain blood flow, and brain magnetic field signal), the pulse rate, myoelectric information, such as myoelectric waveforms, the saliva (such as the amount of saliva), the pulse waves, the blood pressure, the blood flow, the pulse, the heart rate, the electrocardiogram waveforms, the eye movement, the body temperature, the amount of perspiration, gaze, voice, and the motion of a human body. Information obtained by a biomarker may be used as biological information. The above-described items of information are only examples of the biological information, and another item of physiological information or anatomical information may be used as the biological information. The biological information monitoring apparatus 12 may monitor one or multiple items of the above-described items of biological information.

The concept of biological information covers bioelectric potential information indicating the potentials generated from the body. The concept of bioelectric potential information covers brain waves obtained by measuring minute electric currents generated by the brain activities, electrocardiograms created by measuring minute electric currents generated by the heart pulsating beats, electromyograms created by measuring minute electric currents generated by the muscle activities, and skin potentials obtained by measuring minute electric currents generated in the skin. The above-described items of information are only examples of bioelectric potential information, and another item of bioelectric potential information may be used.

After receiving biological information from the biological information monitoring apparatus 12, the information processing apparatus 10 analyzes, stores, and outputs the biological information, and also stores and outputs information indicating the analysis results of the biological information. Analyzing of biological information may alternatively be conducted by the biological information monitoring apparatus 12 or another apparatus. To output biological information is to display it or output it as sound information, for example. To output information indicating the analysis results of biological information is to display it or output it as sound information, for example. The information processing apparatus 10 may send biological information and information indicating the analysis results to another apparatus.

The information processing apparatus 10 may contain one or plural biological information monitoring apparatuses 12. That is, one or plural biological information monitoring apparatuses 12 may be integrated into the information processing apparatus 10 so as to form a single apparatus. The entirety of the information processing apparatus 10 integrating one or plural biological information monitoring apparatuses 12 may be worn by a user to monitor biological information. That is, the information processing apparatus 10 may be a wearable device. Specific examples of the information processing apparatus 10 are a device fixed on the user's head (the forehead, for example), a bearable device attached to the user's ear/ears (such as earphone/earphones, headphones, or a hearing aid), a device fixed to the user's arm, hand, wrist, or finger (for example, a watch-type device, such as a smart watch), a device put on the user's neck, a device fixed to the user's torso (the abdomen or chest, for example), and a device fixed to the lower limb (the thigh, lower leg, knee, foot, or ankle, for example). The information processing apparatus 10 may be health equipment fixed to the user's arm, hand, torso, or lower limb. The information processing apparatus 10 may be attached to another part of the body other than the above-described parts.

The information processing apparatus 10 and the biological information monitoring apparatus 12 may be separate apparatuses. For example, the information processing apparatus 10 may be a device, such as a robot, a smart speaker, or a server, while the biological information monitoring apparatus 12 may be a wearable device worn by a user.

The device 14 has a sound emitting function constituted by a speaker, for example. The device 14 may also have a sound collecting function constituted by a microphone, for example. The device 14 is worn by a user, for example. One or plural devices 14 may be worn by a user. The device 14 may be a bearable device attached to the user's ear/ears (such as earphone/earphones, headphones, or a hearing aid). A hearing aid may be either one of a digital hearing aid and an analog hearing aid. The device 14 may be attached to another part of the body other than the ear. The device 14 may be a device which is not worn by a user, such as a speaker.

One or plural biological information monitoring apparatuses 12 may be integrated into the device 14 so as to form a single apparatus. The entirety of the device 14 integrating one or plural biological information monitoring apparatuses 12 may be worn by a user. For example, the entirety of the device 14 integrating one or plural biological information monitoring apparatuses 12 may be a hearable device.

The information processing apparatus 10, one or plural biological information monitoring apparatuses 12, and one or plural devices 14 may form a single apparatus. The entirety of the single apparatus constituted by the information processing apparatus 10, one or plural biological information monitoring apparatuses 12, and one or plural devices 14 may be worn by a user. For example, this single apparatus may be a hearable device.

Figure 2:
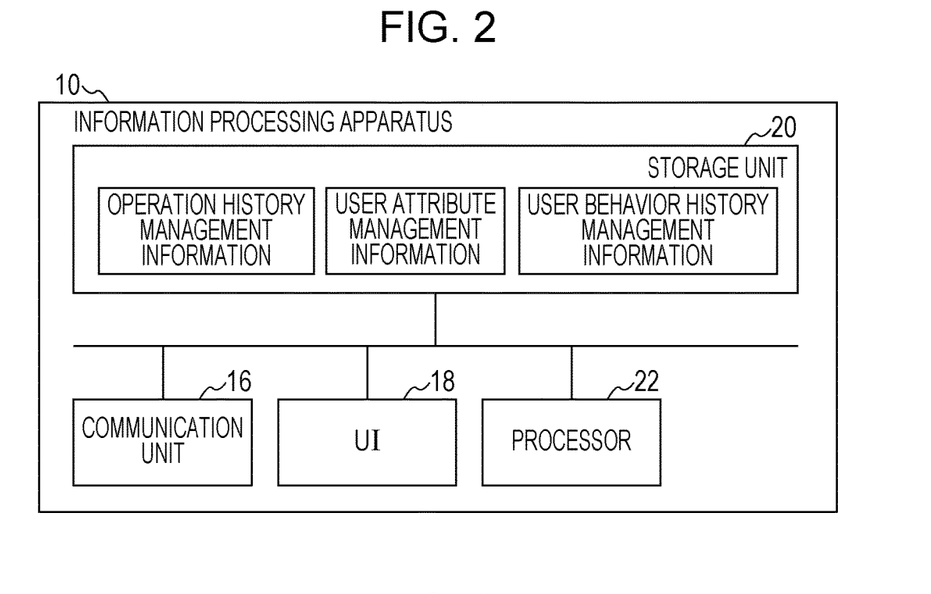
FIG. 2 is a block diagram illustrating an example of the configuration of an information processing apparatus according to the exemplary embodiment.

The configuration of the information processing apparatus 10 will be described below in detail with reference to FIG. 2. FIG. 2 illustrates an example of the configuration of the information processing apparatus 10.

The information processing apparatus 10 includes a communication unit 16, a user interface (UI) 18, a storage unit 20, and a processor 22. The information processing apparatus 10 may include another element other than the above-described elements.

The communication unit 16, which is a communication interface, has a function of sending data to another apparatus and a function of receiving data from another apparatus. The communication unit 16 may have a wireless communication function or a wired communication function. The communication unit 16 may communicate with another apparatus by using short-range wireless communication or via a communication channel, such as a LAN or the Internet. For example, the communication unit 16 receives biological information sent from the biological information monitoring apparatus 12. The communication unit 16 may send control information for controlling the operation of the biological information monitoring apparatus 12 to the biological information monitoring apparatus 12. The communication unit 16 may send control information for controlling the operation of the device 14 to the device 14 and receive information sent from the device 14.

The UI 18 includes at least one of a display and an operation unit. The display is a liquid crystal display or an electroluminescence (EL) display, for example. The operation unit is a keyboard, input keys, or an operation panel, for example. The UI 18 may be a touchscreen which serves both as the display and the operation unit.

The storage unit 20 is a device forming one or multiple storage regions for storing data. The storage unit 20 is a hard disk drive, various memory devices (such as a random access memory (RAM), a dynamic random access memory (DRAM), and a read only memory (ROM)), another storage unit (such as an optical disc), or a combination thereof, for example. One or plural storage units 20 are included in the information processing apparatus 10.

In the storage unit 20, operation history management information, user attribute management information, and user behavior history management information are stored.

The operation history management information is information for managing the operation history of the device 14. The operation history of the device 14 is a history concerning the emission of sound from the speaker of the device 14. The operation history of the device 14 concerns at least one of the total operation time of the device 14, the operation time by volume level, the magnitude of the volume level, the settings of the sound range (for example, the degree of amplitude if the range of higher frequencies or that of lower frequencies is amplified), and the content of sound data (such as music data) played back in the device 14.

For each device 14, device identification information for identifying a device 14 and operation history information indicating the operation history of the device 14 are linked with each other and are registered in the operation history management information. The device identification information is the ID, name, model type, or address (such as media access control (MAC) address or Internet protocol (IP) address) of the device 14, for example.

When the device 14 has started to operate, for example, operation history information indicating the operation history of the device 14 is sent from the device 14 to the information processing apparatus 10 and is registered in the operation history management information. Operation history information may alternatively be stored in the device 14 and be sent from the device 14 to the information processing apparatus 10 and registered in the operation history management information. For example, the device 14 may send operation history information to the information processing apparatus 10 in response to a request from the information processing apparatus 10. The operation history information concerning each device 14 may be managed by another apparatus, such as a server, and the information processing apparatus 10 may obtain the operation history information concerning each device 14 from this apparatus.

The operation history concerning the device 14 may be managed for each user. For example, for each user, user identification information for identifying a user, device identification information concerning the device 14 used by this user, and operation history information concerning the operation history of the device 14 generated by the use of this user are linked with each other and are registered in the operation history management information. The user identification information is the name, ID, email address, or user account of the user, for example.

The operation history management information may not be stored in the storage unit 20 or may be stored in the storage unit 20 and also in another device (such as the device 14 or a server) other than the information processing apparatus 10.

The user attribute management information is information for managing the attributes of a user. The attributes of a user are at least one of the gender, age, medical history, and job history.

For example, for each user, user identification information concerning a user and user attribute information indicating the attributes of the user are linked with each other and are registered in the user attribute management information.

A user may manually input user identification information and user attribute information into the information processing apparatus 10. Alternatively, the information processing apparatus 10 may obtain user identification information and user attribute information from an apparatus (such as a server) that manages the user identification information and user attribute information.

The user attribute management information may not be stored in the storage unit 20 or may be stored in the storage unit 20 and also in another device (such as the device 14 or a server) other than the information processing apparatus 10.

The user behavior history management information is information for managing the history of the behavior of a user. The history of the behavior of a user concerns at least one of drinking, smoking, eating, exercises, medication, sleeping, and other lifestyle habits.

For example, for each user, user identification information concerning a user and behavior history information indicating the history of the behavior of the user are linked with each other and are registered in the user behavior history management information.

A user may manually input user identification information and behavior history information into the information processing apparatus 10. Alternatively, the information processing apparatus 10 may obtain user identification information and behavior history information from an apparatus (such as a server) that manages the user identification information and behavior history information.

The user behavior history management information may not be stored in the storage unit 20 or may be stored in the storage unit 20 and also in another device (such as the device 14 or a server) other than the information processing apparatus 10.

The processor 22 is configured to control the operations of the individual elements of the information processing apparatus 10. The processor 22 may include a memory.

The processor 22 is also configured to execute processing in accordance with the operation history of the device 14 and the judging result regarding whether biological information concerning a user satisfies a condition for hearing loss.

After monitoring biological information concerning a user, the biological information monitoring apparatus 12 sends the biological information to the information processing apparatus 10. The processor 22 receives the biological information and judges whether the biological information satisfies a condition for hearing loss.

Based on the operation history of the device 14 and the judging result regarding whether biological information concerning a user satisfies a condition for hearing loss, the processor 22 judges whether the user has hearing loss and executes processing in accordance with the judging result. There are different types of hearing loss, such as conductive, sensorineural, and mixed hearing loss.

A condition for hearing loss is a condition for determining whether a user has hearing loss, based on biological information.

For example, a condition for hearing loss is a condition for determining whether a user has hearing loss, based on brain waves. A specific example will be given below. The processor 22 judges whether the brain waves of a user satisfy a condition for hearing loss, based on the result of auditory brainstem response (ABR) or auditory steady-state response (ASSR). The processor 22 may notify a user of the judging result regarding whether biological information concerning the user satisfies a condition for hearing loss. For example, the processor 22 may display information concerning the judging result on a display or output sound representing this information from a speaker.

ABR is a test showing how the cochlea and the brainstem auditory pathway are working in response to auditory stimuli. When people hear sound, responses having peaks are normally generated from the cochlea, brainstem, pons, and inferior colliculus. In the normal state, generally five peaks are observed. These peaks are originated from: (wave I) cochlea; (wave II) cochlear nucleus; (wave III) superior olivary complex; (wave IV) lateral lemniscus; and (wave V) inferior colliculus. If these peaks of waveforms are observed with some delay or if the waveforms are disturbed (no peaks are observed, for example), it is judged that the user might have hearing loss.

ASSR is a test utilizing steady-state evoked responses to record potentials generated from the brain in response to auditory stimuli. ASSR enables examination over a broad range of frequencies from the lower frequencies to the higher frequencies.

The processor 22 may analyze brain waves monitored from a user while the device 14 is emitting sound, and judge whether the brain waves satisfy a condition for hearing loss, based on the analysis results. For example, if the brain waves indicate that the user is having difficulty in hearing sound, the processor 22 judges that the brain waves of the user satisfy a condition for hearing loss.

The processor 22 may judge whether biological information concerning a user other than brain waves satisfies a condition for hearing loss. For example, if the blood circulation of the ear is poor or if the blood pressure of the ear indicates an abnormal value, the processor 22 may judge that biological information concerning the user satisfies a condition for hearing loss.

Even if biological information concerning a user satisfies a condition for hearing loss (that is, even if it is judged that the user has hearing loss, based on biological information concerning the user), it does not necessarily mean that the user actually has hearing loss. For example, even if it is judged that a user has hearing loss based on the results of ABR or ASSR, it does not necessarily mean that the user actually has hearing loss. Conversely, even if biological information concerning a user does not satisfy any condition for hearing loss (that is, even if it is judged that the user does not have hearing loss, based on biological information concerning the user), the user may actually have hearing loss.

In the exemplary embodiment, the processor 22 judges whether a user has hearing loss, based on the operation history of the device 14 and the judging result regarding whether biological information concerning the user satisfies a condition for hearing loss. This enhances the precision in determining whether a user has hearing loss, compared with when a judgement is made only based on biological information concerning the user. For example, the device 14 is a bearable device, and the processor 22 judges whether a user has hearing loss, based on the operation history of the device 14 and biological information concerning the user.

The processor 22 may determine to what extent biological information concerning a user satisfies a condition for hearing loss. That is, the processor 22 may determine the degree of hearing loss (the level of hearing loss, for example) based on biological information concerning a user. The level of hearing loss determined based on biological information concerning a user will hereinafter be called "the first level". For example, the processor 22 determines the first level of hearing loss based on the results of ABR or ASSR. The processor 22 may inform the user of the first level of hearing loss. For example, the processor 22 may display information indicating the first level of hearing loss on a display, or output sound representing this information from a speaker.

The processor 22 may determine the degree of hearing loss (the level of hearing loss, for example) based on the operation history of the device 14 and the judging result regarding whether biological information concerning a user satisfies a condition for hearing loss. For example, the processor 22 may determine the degree of hearing loss (the level of hearing loss, for example) of a user, based on the operation history of the device 14 and the degree of hearing loss (the first level, for example) determined based on biological information concerning the user. The level of hearing loss determined based on the operation history of the device 14 and the first level of hearing loss determined based on biological information concerning a user will hereinafter be called "the second level". The processor 22 may inform the user of the second level of hearing loss. For example, the processor 22 may display information indicating the second level of hearing loss on a display, or output sound representing this information from a speaker.

Specific examples of processing to be executed based on the judging result of hearing loss will be discussed below.

An example of processing to be executed based on the judging result of hearing loss is outputting of a caution. That is, the processor 22 may be configured to output a caution, based on the operation history of the device 14 and the judging result regarding whether biological information concerning a user satisfies a condition for hearing loss.

Outputting of a caution is at least one of displaying of information indicating a caution on a display (the display of the UI 18 or that of a user terminal device, for example) and emitting of caution sound from a speaker (the speaker of the device 14 or that of the information processing apparatus 10). For example, the processor 22 may display a message on the display that the volume is too large, the volume needs to be turned down, it is likely that a user will have hearing loss, or a user has hearing loss. The processor may emit sound representing such a message from the speaker.

For example, if it is judged that a user has hearing loss, based on the operation history of the device 14 and the judging result regarding whether biological information concerning the user satisfies a condition for hearing loss, the processor 22 outputs a caution indicating that the user has hearing loss. If it is judged that it is likely that a user will have hearing loss, the processor 22 may output a caution indicating this information. The processor 22 may output a caution indicating the level of hearing loss (first level or second level, for example).

If the volume level of the device 14 is constantly or frequently set as a certain threshold or higher (for example, if the volume level is set as a certain threshold or higher for a predetermined time or longer or a predetermined number of times or greater), the processor 22 may output a caution indicating that the volume is too large or the volume needs to be turned down. If the volume level of the device 14 is set as a certain threshold or higher for only once, the processor 22 may not necessarily output a caution.

Another example of processing to be executed based on the judging result of hearing loss is controlling the volume level of the device 14. That is, the processor 22 may be configured to control the volume level of the device 14, based on the operation history of the device 14 and the judging result regarding whether biological information concerning a user satisfies a condition for hearing loss.

Examples of controlling of the volume level of the device 14 are increasing the volume level, decreasing the volume level, restricting the outputting of a specific sound range, and setting the device 14 in a mute mode.

For example, if it is judged that a user has hearing loss, based on the operation history of the device 14 and the judging result regarding whether biological information concerning the user satisfies a condition for hearing loss, the processor 22 decreases the volume level of the device 14 or sets the device 14 in the mute mode. If it is judged that it is likely that a user will have hearing loss, the processor 22 may decrease the volume level of the device 14. The processor 22 may control the volume level of the device 14 in accordance with the level of hearing loss (first level or second level, for example). For example, the processor 22 may set the volume level of the device 14 to be lower as the level of hearing loss (that is, the degree of hearing loss) is higher.

If the volume level of the device 14 is constantly or frequently set as a certain threshold or higher, the processor 22 may decrease the volume level of the device 14 or set the device 14 in the mute mode. If the volume level of the device 14 is set as a certain threshold or higher for only once, the processor 22 may not necessarily decrease the volume level.

Another example of processing to be executed based on the judging result of hearing loss is controlling of the sound collecting function of the device 14. That is, the processor 22 may be configured to control the sound collecting function of the device 14, based on the operation history of the device 14 and the judging result regarding whether biological information concerning a user satisfies a condition for hearing loss.

Examples of controlling of the sound collecting function of the device 14 are turning ON the sound collecting function, turning OFF the sound collecting function, changing the level of the sound collecting function, turning ON a noise canceling function, and turning OFF the noise canceling function.

For example, if it is judged that a user has hearing loss, based on the operation history of the device 14 and the judging result regarding whether biological information concerning the user satisfies a condition for hearing loss, the processor 22 turns ON the sound collecting function or increases the level of the sound collecting function. The processor 22 may control the sound collecting function of the device 14 in accordance with the level of hearing loss (first level or second level, for example). For example, the processor 22 may set the sound collecting function of the device 14 to be higher as the level of hearing loss (that is, the degree of hearing loss) is higher.

The processor 22 may execute at least one of the operations: outputting a caution, controlling the volume level of the device 14, and controlling the sound collecting function of the device 14. That is, the processor 22 may execute one or multiple operations among the above-described operations. For example, the processor 22 may output a caution and also control the volume level and/or the sound collecting function of the device 14.

Even if the processor 22 controls the volume level or the sound collecting function of the device 14 (increases the volume level or the level of the sound collecting function, for example) for a predetermined time or longer after it is judged that a user has hearing loss, based on the operation history of the device 14 and the judging result regarding whether biological information concerning the user satisfies a condition for hearing loss, the user may still have difficulty in hearing sound. To judge how much the user can hear sound, the processor 22 uses biological information concerning the user. In this case, the processor 22 may output an instruction to use another device 14 which transmits sound via an electric signal. The device 14 which transmits sound via an electric signal uses an electrode to be inserted into the inner ear (cochlea, for example) of a user. An example of such a device 14 is an implant-type hearing aid. As such a device 14, a device which transmits sound to a user by using a combination of electric stimuli and acoustic stimuli may be employed. For example, an electric acoustic stimulation (EAS) device may be used. Even if the volume level is raised or the level of sound collecting function is increased, some people are unable to hear sound correctly because of a large distortion of sound. For such a user, the processor 22 may output an instruction to use a device 14 which transmits sound via an electric signal by using an electrode.

When a user is using the above-described type of device 14, the processor 22 may switch the regular function of the device 14 to the function of transmitting sound via an electric signal by using an electrode if the user still has difficulty in hearing sound.

Processing executed by the processor 22 may be executed by a device other than the information processing apparatus 10, such as a terminal device, a server, the biological information monitoring apparatus 12, or the device 14. Part of processing may be executed by the information processing apparatus 10, and another part of processing may be executed by a device other than the information processing apparatus 10. For example, a device other than the information processing apparatus 10 may analyze biological information, and the information processing apparatus 10 may control the device 14.

Figure 3:
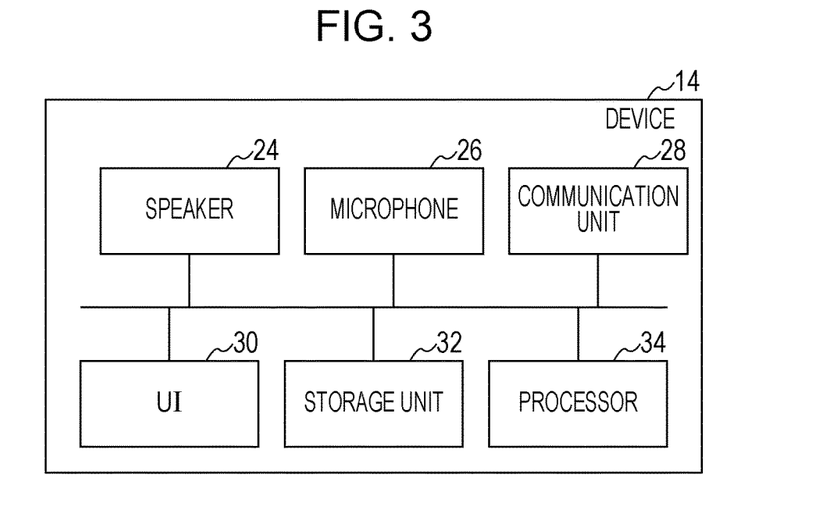
FIG. 3 is a block diagram illustrating an example of the configuration of a device.

The configuration of the device 14 will be described below in detail. FIG. 3 illustrates an example of the configuration of the device 14.

The device 14 includes a speaker 24, a microphone 26, a communication unit 28, a UI 30, a storage unit 32, and a processor 34. The device 14 may include another element other than the above-described elements.

The speaker 24 may emit sound based on sound data or sound collected by the microphone 26. Sound data may be data stored in the storage unit 32 of the device 14 or data sent from the information processing apparatus 10 or another apparatus to the device 14. The microphone 26 has a sound collecting function and collects surrounding sound.

For example, the device 14 may be a hearing aid, an earphone/earphones, or headphones including the speaker 24 and the microphone 26. The device 14 may be a hearing aid which increases the volume level of sound collected by the microphone 26 and emits the sound from the speaker 24. The device 14 may be an earphone/earphones or headphones without the microphone 26.

The communication unit 28, which is a communication interface, has a function of sending data to another device and a function of receiving data from another device. The communication unit 28 may have a wireless communication function or a wired communication function. The communication unit 28 may communicate with another device by using short-range wireless communication or via a communication channel, such as a LAN or the Internet.

The UI 30 includes at least one of a display and an operation unit. The display is a liquid crystal display or an EL display, for example. The operation unit is input keys or an operation panel, for example. The UI 30 may be a touchscreen which serves both as the display and the operation unit.

The storage unit 32 is a device forming one or multiple storage regions for storing data. The storage unit 32 is a hard disk drive, various memory devices (such as a RAM, a DRAM, and a ROM), another storage unit (such as an optical disc), or a combination thereof, for example. One or plural storage units 32 are included in the device 14. Sound data, for example, may be stored in the storage unit 32.

The processor 34 is configured to control the operations of the individual elements of the device 14. The processor 34 may include a memory. For example, the processor 34 emits sound based on sound data from the speaker 24, increases the volume level of sound collected by the microphone 26 and emits the sound from the speaker 24, and controls the volume level of sound emitted from the speaker 24 and/or the sound collecting function of the microphone 26. Instead of the processor 34, the processor 22 of the information processing apparatus 10 may control the volume level and the sound collecting function.

The information processing system according to the exemplary embodiment will be described below in greater detail.

Figure 4:
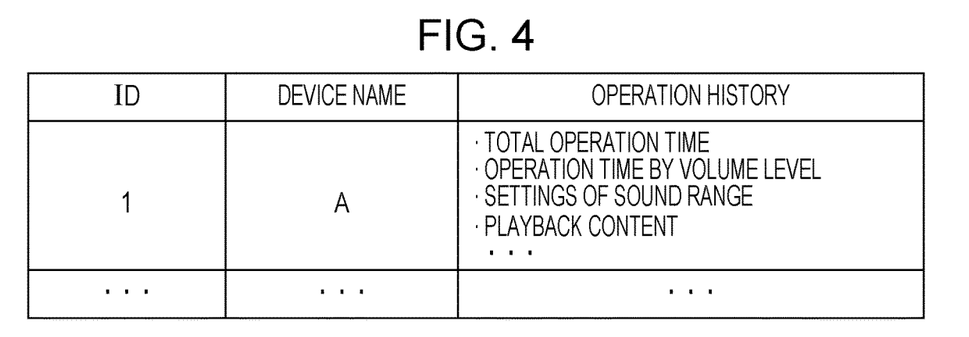
FIG. 4 illustrates an example of an operation history management table.

An example of the operation history management information will be discussed below with reference to FIG. 4. FIG. 4 illustrates an example of an operation history management table, which is an example of the operation history management information. Data in the operation history management table is stored in the storage unit 20. Alternatively, the data in the operation history management table may not be stored in the storage unit 20 or may be stored in the storage unit 20 and also in another device (such as the device 14 or a server) other than the information processing apparatus 10.

In the operation history management table, the ID, device identification information for identifying a device 14, and operation history information indicating the operation history of the device 14, for example, are linked with each other.

Every time the device 14 is in operation, operation history information indicating the history of this operation may be registered in the operation history management table. Alternatively, operation history information concerning each device 14 may be registered in the operation history management table at predetermined regular intervals.

In the example shown in FIG. 4, the operation history information concerning a device A is registered in the operation history management table as the operation history information concerning the ID "1". For example, items of information concerning the total operation time of the device A, the operation time of the device A by volume level of sound emitted from the speaker 24, the settings of the sound range, and the playback content of data (such as music data) are registered in the operation history management table as the operation history information concerning the device A. Operation history information concerning each user may be registered in the operation history management table. Operation history information concerning a device 14 other than the device A is also registered in the operation history management table.

Figure 5:
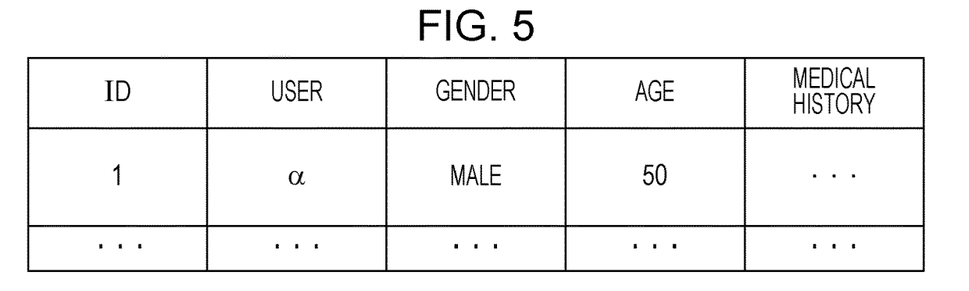
FIG. 5 illustrates an example of a user attribute management table.

An example of the user attribute management information will be discussed below with reference to FIG. 5. FIG. 5 illustrates an example of a user attribute management table, which is an example of the user attribute management information. Data in the user attribute management table is stored in the storage unit 20. Alternatively, the data in the user attribute management table may not be stored in the storage unit 20 or may be stored in the storage unit 20 and also in another device (such as a server or a user terminal device) other than the information processing apparatus 10.

In the user attribute management table, the ID, user identification information for identifying a user, and user attribute information concerning the attributes of this user, for example, are linked with each other.

In the example shown in FIG. 5, user attribute information concerning a user a is registered in the user attribute management table as the user attribute information concerning the ID "1". For example, items of information indicating the gender, age, and medical history concerning the user a are registered in the user attribute management table as the user attribute information concerning the user a. User attribute information concerning a user other than the user a is also stored in the user attribute management table.

Figure 6:
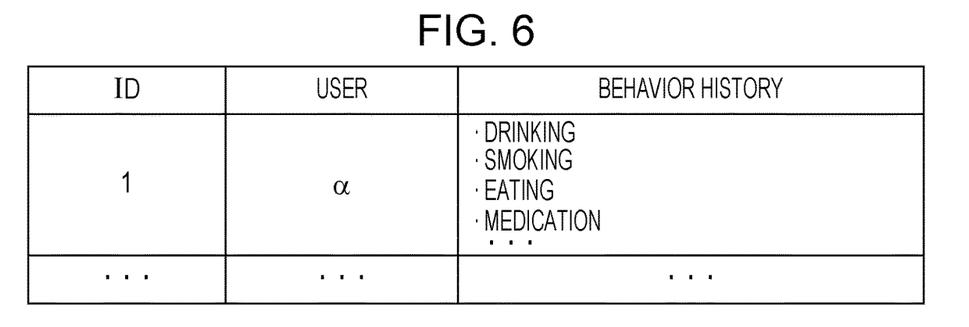
FIG. 6 illustrates an example of a user behavior history management table.

An example of the user behavior history management information will be discussed below with reference to FIG. 6. FIG. 6 illustrates an example of a user behavior history management table, which is an example of the user behavior history management information. Data in the user behavior history management table is stored in the storage unit 20. Alternatively, the data in the user behavior history management table may not be stored in the storage unit 20 or may be stored in the storage unit 20 and also in another device (such as a server or a user terminal device) other than the information processing apparatus 10.

In the user behavior history management table, the ID, user identification information for identifying a user, and behavior history information concerning the history of the behavior of this user, for example, are linked with each other.

In the example shown in FIG. 6, behavior history information concerning the user α is registered in the user behavior history management table as the behavior history information concerning the ID "1". For example, items of history information concerning drinking, smoking, eating, and medication of the user α are registered in the user behavior history management table as the behavior history information concerning the user α. Behavior history information concerning a user other than the user a is also registered in the user behavior history management table.

Figure 7:
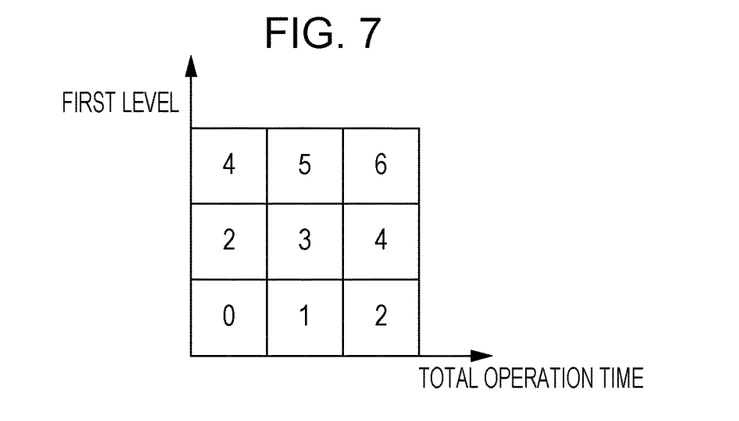
FIG. 7 is a diagram illustrating the level of hearing loss.

The level of hearing loss will be explained below with reference to FIG. 7. FIG. 7 is a diagram illustrating the level of hearing loss. The horizontal axis indicates the total operation time of the device 14, which is an example of the operation history of the device 14. The vertical axis indicates the first level of hearing loss determined based on biological information concerning a user. The first level is the level of hearing loss determined based on the results of ABR or ASSR, for example.

Each numerical value shown in FIG. 7 represents the second level of hearing loss determined based on the total operation time of the device 14 and the first level of hearing loss. A greater numerical value represents a high degree of hearing loss. For example, the second level "0" indicates that the degree of hearing loss is the lowest level. The second level "1" indicates that the degree of hearing loss is higher than the second level "0" and is lower than the second level "2".

As the total operation time of the device 14 is longer, the second level of hearing loss becomes higher. As the first level of hearing loss is higher, the second level of hearing loss becomes higher. That is, as the level of hearing loss determined based on biological information concerning a user (that is, the first level) is higher, the second level of hearing loss becomes higher.

The processor 22 obtains the operation history information concerning the device 14 from the operation history management table, determines the first level based on biological information concerning a user, and then determines the second level of hearing loss based on the association between the operation history information and the first level shown in FIG. 7. For example, if the second level is lower than a first threshold, the processor 22 judges that the user does not have hearing loss. If the second level is higher than or equal to the first threshold and is lower than a second threshold which is greater than the first threshold, the processor 22 judges that the user might have hearing loss. If the second level is higher than the second threshold, the processor 22 judges that the user has hearing loss. This approach to making a judgement about hearing loss is only an example, and a judgement may be made by another approach. For example, if the second level is "0", the processor 22 judges that the user does not have hearing loss. If the second level is "1", "2", or "3", the processor 22 judges that the user might have hearing loss. If the second level is "4" or greater, the processor 22 judges that the user has hearing loss.

Instead of or in addition to the total operation time, another operation history may be used. That is, the parameter represented by the horizontal axis in FIG. 7 may be at least one of the total operation time, the operation time by volume level, the magnitude of the volume level, the settings of the sound range, and the playback content of sound data.

For example, the magnitude of the volume level may be used as the operation history. As the magnitude of the volume level is larger, the second level of hearing loss becomes higher.

The settings of the sound range may alternatively be used as the operation history. For example, if the range of higher frequencies is amplified for a user, the processor 22 judges that the user has difficulty in hearing sound in the range of higher frequencies and may determine the second level of hearing loss regarding the range of higher frequencies. For example, as the range of higher frequencies is amplified by a greater amount, the second level of hearing loss regarding the range of higher frequencies becomes higher. Regarding the range of lower frequencies, the second level may be determined in a similar manner.

Multiple items of histories may be used as the operation history. For example, the total operation time and the magnitude of the volume level may be used as the operation history. For example, if sound is emitted from the device 14 at a certain volume level or higher for a certain period of time or longer, it can be predicted that using the device 14 in this manner will make a user vulnerable to having hearing loss. In this case, the second level of hearing loss becomes higher than that when the device 14 is not used in this manner.

The processor 22 may make a judgement regarding whether a user has hearing loss, based on the attributes of the user, the operation history of the device 14, and the judging result regarding whether biological information concerning the user satisfies a condition for hearing loss. The processor 22 obtains attribute information concerning the user from the user attribute management table and also obtains the operation history information concerning the device 14 from the operation history management table.

An example of the attributes of the user is the user's age. For example, as the age is older, the second level of hearing loss becomes higher. The processor 22 may also determine based on the user's age whether the user has hearing loss because of aging. For example, if the user's age is higher than or equal to a threshold for the age and if the second level of hearing loss is higher than or equal to a threshold for the second level, the processor 22 may determine that the user has hearing loss because of aging.

The attributes of a user may the age of the user, and the operation history of the device 14 may be the history of the settings of the sound range set by this user. For example, if the user's age is higher than or equal to a threshold for the age and if the range of higher frequencies is amplified, the processor 22 may determine that the user has hearing loss regarding the range of higher frequencies. When people become fifty or older, they may have difficulty in hearing sound in the range of higher frequencies. Hence, if the user's age is fifty or older and if the range of higher frequencies is amplified, the processor 22 determines that the user is hard of hearing regarding the range of higher frequencies. Higher frequencies in this range are determined in advance.

Another example of the attributes of a user is a medical history of the user. People may have hearing loss (sensorineural hearing loss, for example) as a consequence of their diseases. Examples of diseases that may cause hearing loss are acoustic neuroma, cholesteatoma, Ménière's disease, meningitis, otosclerosis, Down syndrome, and Treacher Collins syndrome. If the medical history of a user indicates a disease that may cause hearing loss, the second level becomes higher than when the medical history of a user does not indicate such a disease. For example, even if the operation history of the device 14 used by a user having a disease that may cause hearing loss and that by a user without having such a disease are the same, the second level for the user with such a disease becomes higher than the user without such a disease. Likewise, even if the first level for a user having a disease that may cause hearing loss and that for a user without having such a disease are the same, the second level for the user with such a disease becomes higher than the user without such a disease.

The processor 22 may make a judgement regarding whether a user has hearing loss, based on the history of the behavior of the user, the operation history of the device 14, and the judging result regarding whether biological information concerning the user satisfies a condition for hearing loss. The processor 22 obtains behavior history information concerning the user from the user behavior history management table and also obtains the operation history information concerning the device 14 from the operation history management table.

For example, alcohol consumption or smoking impairs the blood circulation and may cause sudden sensorineural hearing loss. For example, as the alcohol intake is larger, the second level of hearing loss becomes higher, and as the amount of smoking is greater, the second level of hearing loss becomes higher.

Lack of sleep may also cause hearing loss. For example, if sleeping hours are out of a predetermined time range, the second level of hearing loss becomes higher than when sleeping hours are within the predetermined time range. The predetermined time range is a range of times which makes it less likely to have hearing loss. If the quality of sleep is poor, the second level of hearing loss becomes higher than when the quality of sleep is good.

Some dietary habits may also cause hearing loss. Dietary habits, calorie intake, and nutrition facts, for example, that may cause hearing loss are determined in advance. As a user is more dependent on such a diet, the second level of hearing loss becomes higher.

Some lifestyle habits may also cause hearing loss. For example, lifestyle habits that may cause hearing loss are determined in advance. The second level of hearing loss for a user having such a lifestyle habit becomes higher than a user without it.

Medication may also cause hearing loss. The second level of hearing loss for a user being on medication is higher than a user which is not on medication. Certain types of medication that make it more likely to cause hearing loss are determined in advance. The second level of hearing loss for a user being on such a type of medication becomes higher than a user who is not on such a type of medication.

The second level determined by the association shown in FIG. 7 is only an example. The second level may be determined by an approach other than that represented by the association in FIG. 7. For example, the second level may be determined by the use of a function. For example, a function using the operation history of the device 14 and the first level as parameters may be used to determine the second level. A function using the attributes of a user and the history of the behavior of the user as parameters may be used to determine the second level.

The processor 22 may execute a function of helping a user recover from hearing loss (hereinafter such a function will be called the hearing-loss recovery function). For example, if it is judged that a user has hearing loss (for example, when the second level is higher than or equal to a threshold), the processor 22 may execute the hearing-loss recovery function. If it is judged that it is likely that a user will have hearing loss (for example, if an element that may cause hearing loss is found although the second level is lower than the threshold), the processor 22 may also execute the hearing-loss recovery function.

Examples of the hearing-loss recovery function are a function of relieving stress or eliminating fatigue from a user, a function of improving the blood circulation, and a function of encouraging a user to reconsider its behavior. Examples of the function of relieving stress or eliminating fatigue from a user are a function of playing music that can make a user feel relaxed and a function of proposing a diet that can help a user recover from fatigue. Examples of the function of improving the blood circulation are a function of warming the user's ear, a function of playing music that can enhance the blood circulation, and a function of suggesting a diet that can enhance the blood circulation. For example, the device 14 is a bearable device (a hearing aid, an earphone/earphones, or headphones) having a warming function. The device 14 is attached to the user's ear, which can be warmed, thereby enhancing the blood circulation. B vitamins ($B_{12}$, for example) serve to help a user recover from peripheral neuropathy. The processor 22 may propose a diet having a high content of B vitamins to the user. Examples of the function of encouraging a user to reconsider its behavior are a function of encouraging a user to quit a lifestyle habit that may cause hearing loss and a function of introducing lifestyle habits that can help a user recover from hearing loss.

The hearing-loss recovery function may be a noise canceling function. For example, the device 14 is a hearable device (a hearing aid, an earphone/earphones, or headphones, for example) having a noise canceling function, and is attached to the user's ear. Executing the noise canceling function can eliminate surrounding noise. Even if the volume level of a hearable device (a hearing aid, an earphone/earphones, or headphones, for example) is turned down, using the noise canceling function enables a user to hear sound emitted from the hearable device better than when the noise canceling function is not executed.

The hearing-loss recovery function may be a function of turning down the volume level of a hearable device (a hearing aid, an earphone/earphones, or headphones, for example). The processor 22 may turn down the volume level as well as executing the noise canceling function.

Normalizing the balance in the autonomic nervous system (sympathetic nervous system and parasympathetic nervous system, for example) may maintain user's hearing or help a user recover from hearing loss. The processor 22 may suggest how to normalize the balance in the autonomic nervous system to a user.

The processor 22 may simultaneously execute multiple hearing-loss recovery functions. The processor 22 may alternatively execute one of the hearing-loss recovery functions for a predetermined time and, when it has finished executing this function, it may execute another function for a predetermined time.

The processor 22 may execute a hearing-loss recovery function in response to an instruction from a user. For example, the processor 22 may perform control to display information concerning multiple hearing-loss recovery functions on the display of the UI 18 or the display of a user terminal device. When a user has selected one of the functions, the processor 22 executes the selected function. The processor 22 may alternatively execute a hearing-loss recovery function without receiving an instruction from a user.

The processor 22 may estimate how much a user has recovered from hearing loss, based on biological information concerning the user. For example, the processor 22 may estimate how much a user has recovered from hearing loss (in other words, the current degree of hearing loss), based on the results of ABR or ASSR or in accordance with whether brain waves, which are an example of biological information, indicate that the user is having difficulty in hearing. Based on the estimated degree of hearing loss (how much the user has recovered from hearing loss), the processor 22 may change the execution time of a hearing-loss recovery function, repeatedly execute the same hearing-loss recovery function, switch to another hearing-loss recovery function, or additionally execute another hearing-loss recovery function.

The processor 22 may estimate the reason why a user has had hearing loss, based on the attributes of the user, the history of the behavior of the user, and the operation history of the device 14, and execute a hearing-loss recovery function in accordance with the estimated reason. For example, if the processor 22 has estimated that user's hearing has deteriorated because of the user's eating habits, it suggests a diet that can help the user recover from hearing loss. If the processor 22 has estimated that user's hearing has deteriorated because of lack of sleep, it recommends that the user sleep for longer hours. If the processor 22 has estimated that user's hearing has deteriorated because of drinking or smoking, it recommends that the user reduce alcohol intake or the amount of smoking.

When it is judged that a user has hearing loss and if the type of hearing loss (conductive, sensorineural, or mixed hearing loss, for example) is estimated, the processor 22 may display information indicating the type of hearing loss or output sound indicating this information. The processor 22 may execute a hearing-loss recovery function in accordance with the type of hearing loss. For example, sensorineural hearing loss may develop because of the problem in the inner ear. If a user has sensorineural hearing loss, the processor 22 may execute a hearing-loss recovery function effective for the inner ear. Conductive hearing loss may develop because of the problem in a portion somewhere from the outer ear to the middle ear. If a user has conductive hearing loss, the processor 22 may execute a hearing-loss recovery function effective for the portion from the outer ear to the middle ear. The processor 22 may present a hearing-loss recovery function to a user in accordance with the type of hearing loss.

In the embodiment above, the term "processor" refers to hardware in a broad sense. Examples of the processor includes general processors (e.g., CPU: Central Processing Unit), dedicated processors (e.g., GPU: Graphics Processing Unit, ASIC: Application Integrated Circuit, FPGA: Field Programmable Gate Array, and programmable logic device). In the embodiment above, the term "processor" is broad enough to encompass one processor or plural processors in collaboration which are located physically apart from each other but may work cooperatively. The order of operations of the processor is not limited to one described in the embodiment above, and may be changed.

The foregoing description of the exemplary embodiment of the present disclosure has been provided for the purposes of illustration and description. It is not intended to be exhaustive or to limit the disclosure to the precise forms disclosed. Obviously, many modifications and variations will be apparent to practitioners skilled in the art. The embodiment was chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. An information processing apparatus comprising:
 a processor configured to
   output a caution, based on an operation history of a device, the device being worn by a user and emitting sound, and on a judging result regarding whether biological information concerning the user satisfies a condition for hearing loss,
 wherein the biological information concerning the user is brain waves of the user, and the processor is further configured to:
   store, in a memory, an operation time of the device,
   judge a level of hearing loss based on the brain waves of the user,
   adjust the judged level of hearing loss of the user based on the operation history of the device within a predetermined time that is read from the memory, and
   indicate the adjusted level of hearing loss of the user.

2. The information processing apparatus according to claim 1, wherein the processor is further configured to determine whether the user has hearing loss, based on an attribute of the user, the operation history of the device, and the judging result.

3. The information processing apparatus according to claim 2, wherein:
the attribute of the user is the age of the user; and
the operation history of the device is a history concerning a setting of a sound range set by the user.

4. The information processing apparatus according to claim 2, wherein the attribute of the user is a medical history of the user.

5. The information processing apparatus according to claim 1, wherein the processor is further configured to determine whether the user has hearing loss, based on a history of behavior of the user, the operation history of the device, and the judging result.

6. The information processing apparatus according to claim 1, wherein
the processor judges whether the brain waves of the user satisfy the condition for hearing loss, based on a result of auditory brainstem response or auditory steady-state response.

7. The information processing apparatus according to claim 1, wherein
the processor judges that the brain waves of the user satisfy the condition for hearing loss when the brain waves indicate that the user is having difficulty in hearing sound emitted from the device.

8. The information processing apparatus according to claim 1, wherein the processor is further configured to execute a hearing-loss recovery function of helping the user recover from hearing loss when the processor has determined that the user has hearing loss.

9. The information processing apparatus according to claim 8, wherein:
the device is attached to an ear of the user; and
the hearing-loss recovery function is a function of warming the ear of the user.

10. The information processing apparatus according to claim 8, wherein:
the device is attached to an ear of the user; and
the hearing-loss recovery function is a noise canceling function.

11. An information processing apparatus comprising:
a processor configured to
control a sound collecting function of a device, the device being worn by a user and having a sound emitting function and the sound collecting function, based on an operation history of the device and on a judging result regarding whether biological information concerning the user satisfies a condition for hearing loss,
wherein the biological information concerning the user is brain waves of the user, and the processor is further configured to:
store, in a memory, an operation time of the device,
judge a level of hearing loss based on the brain wave of the user,
adjust the judged level of hearing loss of the user based on the operation history of the device within a predetermined time that is read from the memory, and
indicate the adjusted level of hearing loss of the user.

12. The information processing apparatus according to claim 11, wherein the processor is further configured to determine whether the user has hearing loss, based on an attribute of the user, the operation history of the device, and the judging result.

13. The information processing apparatus according to claim 12, wherein:
the attribute of the user is the age of the user; and
the operation history of the device is a history concerning a setting of a sound range set by the user.

14. The information processing apparatus according to claim 12, wherein the attribute of the user is a medical history of the user.

15. The information processing apparatus according to claim 11, wherein the processor is further configured to determine whether the user has hearing loss, based on a history of behavior of the user, the operation history of the device, and the judging result.

16. The information processing apparatus according to claim 11, wherein
the processor judges whether the brain waves of the user satisfy the condition for hearing loss, based on a result of auditory brainstem response or auditory steady-state response.

17. The information processing apparatus according to claim 11, wherein the processor judges that the brain waves of the user satisfy the condition for hearing loss when the brain waves indicate that the user is having difficulty in hearing sound emitted from the device.

18. The information processing apparatus according to claim 11, wherein the processor is further configured to execute a hearing-loss recovery function of helping the user recover from hearing loss when the processor has determined that the user has hearing loss.

19. A method comprising:
by a processor,
outputting a caution, based on an operation history of a device, the device being worn by a user and emitting sound, and on a judging result regarding whether biological information concerning the user satisfies a condition for hearing loss, wherein the biological information concerning the user is brain waves of the user,
storing, in a memory, an operation time of the device,
judging a level of hearing loss based on the brain waves of the user,
adjusting the judged level of hearing loss of the user based on the operation history of the device within a predetermined time that is read from the memory, and
generating a behavior recommendation based on the adjusted level of hearing loss of the user.

20. The method of claim 19, further comprising: by the processor, informing the user the behavior recommendation.

* * * * *